United States Patent

Smith

[11] Patent Number: 5,938,647
[45] Date of Patent: Aug. 17, 1999

[54] OSTOMY BAG LINER

[75] Inventor: Rory James Maxwell Smith, Nr. Skipton, United Kingdom

[73] Assignee: Welland Medical Limited, West Sussex, United Kingdom

[21] Appl. No.: 08/765,605

[22] PCT Filed: Jun. 19, 1995

[86] PCT No.: PCT/GB95/01424

§ 371 Date: Dec. 31, 1996

§ 102(e) Date: Dec. 31, 1996

[87] PCT Pub. No.: WO96/01090

PCT Pub. Date: Jan. 18, 1996

[30] Foreign Application Priority Data

Jul. 1, 1994 [GB] United Kingdom .................. 9413231

[51] Int. Cl.⁶ .................................................. A61F 5/445
[52] U.S. Cl. .................................. 604/332; 128/DIG. 24
[58] Field of Search ...................................... 604/332, 338; 128/DIG. 24

[56] References Cited

U.S. PATENT DOCUMENTS

| 3,665,923 | 5/1972 | Champaigne, Jr. ............... 604/364 |
| 4,203,445 | 5/1980 | Jessup et al. .................... 128/283 |
| 4,230,761 | 10/1980 | Watts ............................. 428/215 |
| 4,946,720 | 8/1990 | Oishi et al. ..................... 604/332 |
| 5,108,382 | 4/1992 | Wright et al. .................... 604/342 |

FOREIGN PATENT DOCUMENTS

| 0 226 439 | 6/1987 | European Pat. Off. . |
| 0 259 184 | 3/1988 | European Pat. Off. . |
| 0 273 611 | 7/1988 | European Pat. Off. . |
| 0 388 924 | 9/1990 | European Pat. Off. . |
| 0 475 608 | 3/1992 | European Pat. Off. . |
| 0 476 847 | 3/1992 | European Pat. Off. . |
| 2 385 598 | 10/1978 | France . |
| 2 638 634 | 5/1990 | France . |
| 2 083 762 | 3/1982 | United Kingdom . |
| 2 099 753 | 12/1982 | United Kingdom . |
| 2 211 196 | 6/1989 | United Kingdom . |
| 2 226 761 | 7/1990 | United Kingdom . |
| 2 273 052 | 6/1994 | United Kingdom . |
| WO 89/11262 | 11/1989 | WIPO . |
| WO 94/12128 | 6/1994 | WIPO . |

*Primary Examiner*—Robert A. Clarke
*Attorney, Agent, or Firm*—Lahive & Cockfield, LLP; Anthony A. Laurentano

[57] ABSTRACT

The invention provides a biodegradable, flushable ostomy bag liner including: inner walls (3, 4) formed from polyvinylacetate/polyvinylalcohol film of a grade which disintegrates within 60 seconds in water at 50° C., but retains its structural integrity in water at 25° C. for at least two days; outer walls (1, 2) formed from a non-woven fabric which disintegrates in water at 25° C.; structure defining an opening (8) in the inner and outer walls for receiving bodily waste from the stoma of a patient; and adhesive flange (7) for securing the ostomy bag liner to the body wall of a patient, the adhesive flange (7) being secured to at least an inner wall (1) of the liner and surrounding the said opening (8); wherein the inner and outer walls (1, 2, 3, 4) are unconnected and form an non-laminar arrangement over the greater part of their area, but are connected together around their peripheral margins (5) and in the region of the adhesive flange (7).

16 Claims, 2 Drawing Sheets

OSTOMY BAG LINER

REFERENCE TO RELATED APPLICATIONS

This application is the National Stage of International Application No. PCT/GB95/01424, filed Jun. 19, 1995.

BACKGROUND OF THE INVENTION

This invention relates to a biodegradable, flushable, ostomy bag liner.

Ostomy bags for receiving bodily waste from colostomy or ileostomy patients are well known and a major problem with such bags is that it can be difficult to dispose of the used bag in a convenient and hygienic manner. Often, the contents of used bags are removed by cutting an edge of the bag and depositing the contents into a W.C. for flushing away, leaving the soiled bag for separate disposal, e.g. by incineration or by wrapping and placing in a waste bin. Disposal of a used bag and its contents in this way is clearly unhygienic and unpleasant for the user, and, in recognition of this problem, various proposals have been made for ostomy bags which can be flushed down a W.C.:—see for example GB-A-2083762, EP-A-0388924, GB-A-2227668, and GB-A-2193925. Many of the known types of disposable ostomy bag currently available suffer from certain drawbacks. Firstly, due to the buoyancy and relative bulk of the bags, it is often difficult to flush them down a W.C. Secondly, in order to ensure that the bag is sufficiently strong and waterproof to withstand the rigours of use, materials have been used which do not decompose readily, if at all, in the sewerage system, thereby giving rise to a pollution problem.

Our earlier Application WO-A-94/12128, the contents of which are incorporated by reference herein, seeks to overcome such problems by providing a relatively tough, waterproof detachable outer bag, and a water-impermeable inner bag or liner, the inner bag serving to accommodate the bodily waste whilst the outer bag serves as a protective layer. The inner bag is made sufficiently water-impermeable to prevent leakage into the outer bag during a period of use but, because of the existence of the outer bag, need not be made of such durable material. Thus, it can be made of material which although water-impermeable over a short period, nonetheless gradually dissolves over a more extended period. The inner bag can therefore be made entirely biodegradable and is ideally suited for disposal by flushing down a W.C. The outer bag which is secured to the inner bag by means of a frangible or peelable connection is torn away from the inner bag after use and, since it is not soiled by the bodily waste, can be disposed of with other household refuse.

SUMMARY OF THE INVENTION

The present invention is concerned principally, although not exclusively, to improvements in the construction of inner bags suitable for use in the two-bag system disclosed in WO-A-94/12128.

Accordingly, in a first aspect, the invention provides a biodegradable, flushable ostomy bag liner comprising:

inner walls formed from polyvinylacetate/polyvinylalcohol film of a grade which disintegrates within 60 seconds in water at 50° C., but retains its structural integrity in water at 25° C. for at least two days;

outer walls formed from a non-woven fabric which disintegrates in water at 25° C.;

means defining an opening in the inner and outer walls for receiving bodily waste from the stoma of a patient;

an adhesive flange for securing the ostomy bag liner to the body wall of a patient, the adhesive flange being secured to at least an inner wall of the liner and surrounding the said opening; wherein the inner and outer walls are unconnected and form a non-laminar arrangement over the greater part of their area, but are connected together around their peripheral margins and in the region of the adhesive flange.

The non-woven fabric is preferably formed from biodegradable fibres. Typically the fibres making up the non-woven fabric will have an average length of less than 8 mm, preferably less than 6 mm, and more preferably approximately 5 mm.

The non-woven fabric may contain cellulose based fibres and a water-soluble/water-disintegrable polymer capable of binding the fibres. An example of a water-soluble/water-disintegrable polymer suitable for this use is PVA which may be in fibre form. Examples of cellulose based fibres are fibres formed from rayon, cellulose acetate, or cotton.

The cellulose fibres can be present in a ratio of at least 5:1 weight ratio with regard to the polymeric binder, more preferably at least 10:1, for example approximately 20:1.

Instead of cellulosic fibres, wholly synthetic fibres such as polyester fibres, or a blend of cellulosic and synthetic fibres, may be used.

The non-woven fabric may conveniently be made on paper making apparatus by mixing together the fibres and polymeric binder in the form of an aqueous slurry and depositing the slurry on to a water-pervious moving conveyor, removing water from the slurry by drawing it through the conveyor, and transporting the mixture through an oven to cure the mixture.

If a non-woven fabric of the aforementioned type comes into contact with water, the polymeric binder dissolves, thereby destroying the binder-cellulosic fibre bond, and the fabric falls apart.

The inner walls of the liner typically are constituted by a pair of sheets of the polyvinylacetate/polyvinylalcohol film welded or adhesively secured together around their peripheral margins. The outer walls of the liner are constituted by a pair of sheets of the non-woven material which are secured, e.g. by welding or adhesive bonding, to the outer surfaces of the inner walls (e.g. the PVA film) at the peripheral margins. The inner and outer walls are also connected together, in the region of the adhesive flange. For example, they may be connected together by virtue of both being secured (e.g. by welding or adhesive bonding) to the rear surface of the adhesive flange. However, between the area of connection on the adhesive flange, and the peripheral margins of the ostomy bag, the inner and outer walls are substantially unconnected.

The inner and outer walls are preferably formed of such material, and have such thickness, as to be of substantially equivalent mechanical strength. In the present context, the term "substantially equivalent mechanical strength" means that the tensile strengths of the two walls in the dry state differ by no more than about 20%.

BRIEF DESCRIPTION THE DRAWINGS

An embodiment of the present invention will now be illustrated by reference to the accompanying drawings in which.

DESCRIPTION OF ILLUSTRATED EMBODIMENT

Figure 1:
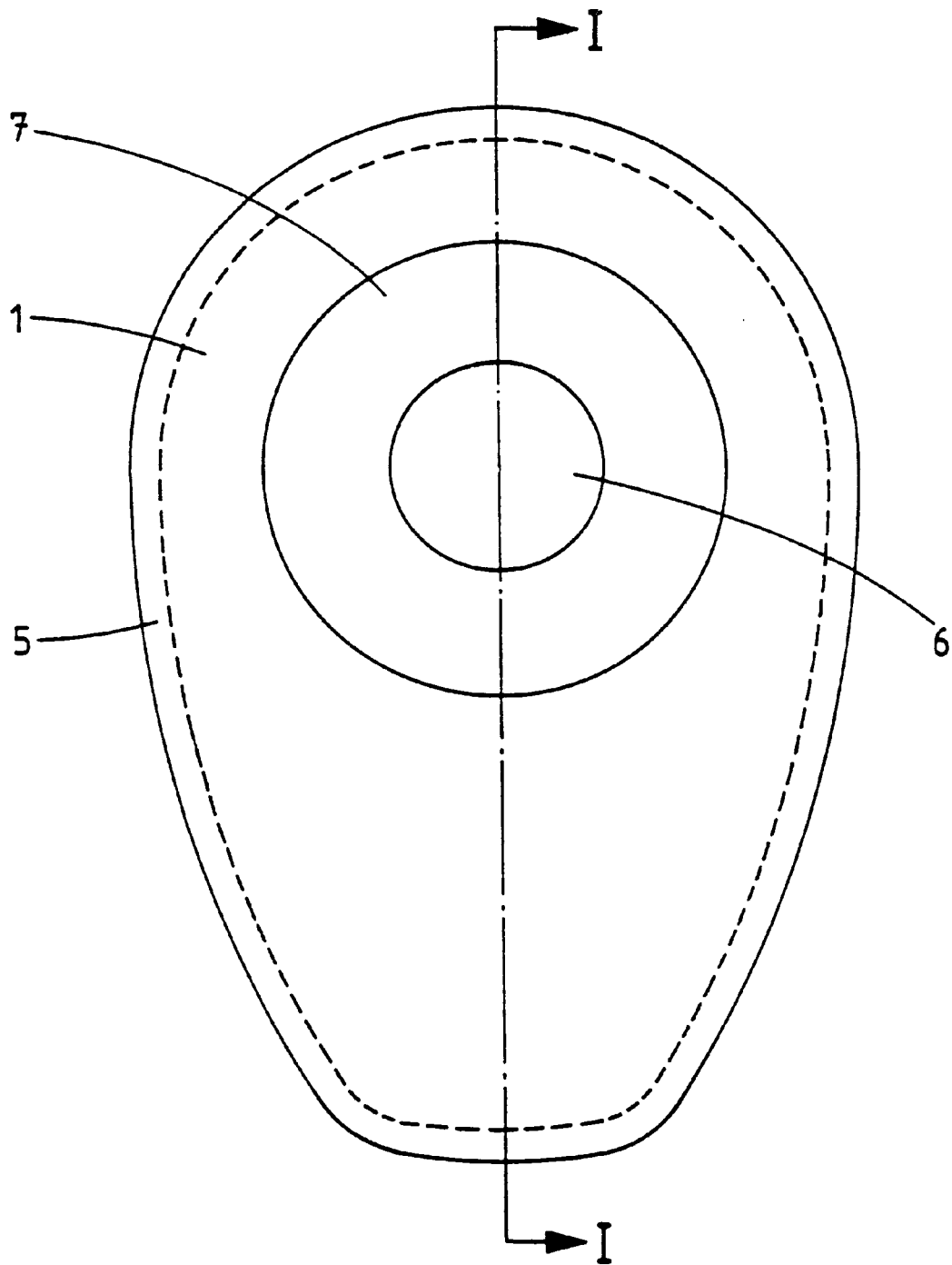
FIG. 1 is a plan view of an ostomy bag liner according to one embodiment of the present invention.

Referring now to the drawings, it can be seen that an ostomy bag liner according to the present invention comprises outer walls 1, 2 and, enclosed therein, inner walls 3, 4. Inner walls 3, 4 are sealed together by heat welding at the peripheral margin 5, outer walls 1, 2 being welded to the outer surfaces of the inner walls 3, 4, also at the peripheral margins.

The liner has an opening 6 through which the stoma (not shown) of a patient may protrude. In order to secure the liner to a body wall of the patient, an adhesive flange 7 is provided.

The inner wall 3 and outer wall 1 are each secured to the rear surface of adhesive flange 7, the inner wall 3 being secured to the flange at a position radially inwardly of the outer wall 1.

The liner is also provided with a flatus gas venting system comprising an opening 8 in the inner wall 3 which is covered by a disc 9 of gas-permeable hydrophobic polyurethane foam material. Outer wall 1, being of a fibrous nature rather than being in the form of a film, is fully permeable to gases.

The outer walls 1, 2 are formed from a non-woven material comprising rayon fibres and PVA in the ratio 20:1. The rayon fibres are chosen such that the average length of the fibres is less than 8 mm, preferably less than 6 mm long, and more preferably approximately 5 mm long. The non-woven material is made by mixing the fibres together with PVA fibres and an appropriate amount of water to form a slurry. The PVA fibres can be "Mewlon" (TM) fibres of grade SMB or SML available from Unikita Ltd. In the fibrous form the "Mewlon" PVA dissolves at around 65°–70° C. but when formed into the non-woven material, dissolves rapidly in cold water. The PVA fibre/rayon slurry is deposited on to a water-pervious moving conveyor, and then partially dried by drawing water through holes in the water-pervious conveyor. The resulting partially dried web is then passed through an oven set at about 100° C. to cure the mixture.

In the resulting non-woven material product, the PVA serves to bind the rayon fibres together. However, once the non-woven material comes into contact with water, the PVA dissolves or disintegrates, thereby destroying the bonding between adjacent rayon fibres with the result that the non-woven fabric rapidly disintegrates.

The inner walls 3, 4 in this embodiment are formed of a 30 $\mu$ thick PVA film of a grade which is rapidly soluble in hot water, i.e. dissolves or disintegrates within 30 seconds at 50° C. in water, but at 38° C. is only very slowly soluble, and at room temperature is reasonably stable. An example of such a film is EC600 grade film available from NEDI Middlewich, Cheshire, UK. Such film is not only soluble in hot water, but is also degraded by bacteria relatively quickly.

Figure 3:
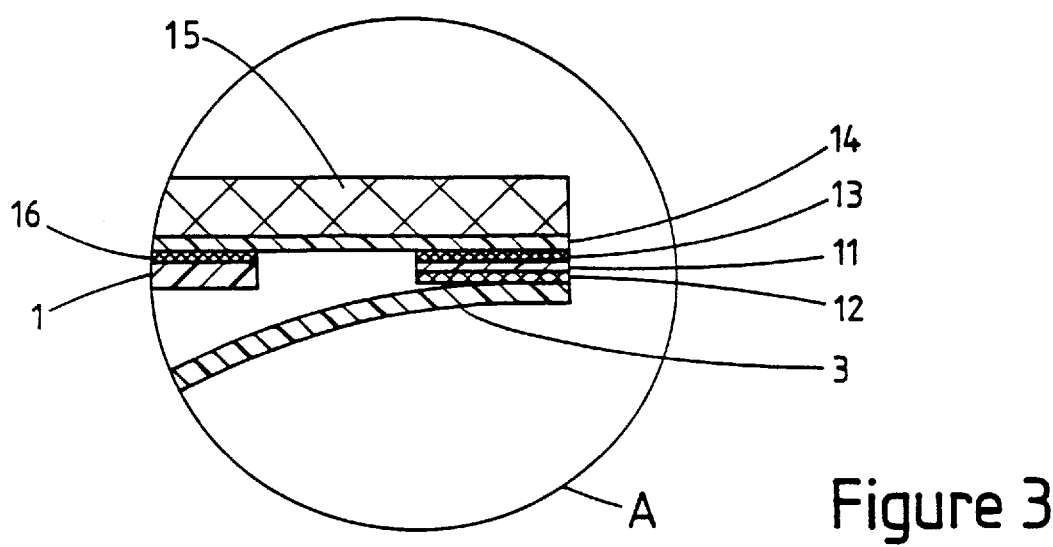
FIG. 3 is an enlarged view of the region marked A in FIG. 2.

The manner in which the inner wall 3 is secured to the adhesive flange is shown in more detail in FIG. 3. From FIG. 3, it can be seen that the inner wall 3 is secured to an intermediate layer 11 of polyvinylchloride (PVC) film by means of intervening layer 12 of cyanoacrylate adhesive, and thence by adhesive layer 13 to PVC backing film 14 of the adhesive flange. Backing film 14 is coated with a thick layer of hydrocolloid adhesive 15 of known type. The adhesive layer 13 may be, for example, either a rubber resin or an acrylic-based adhesive.

The outer wall 1 of non-woven fabric, is secured to the PVC backing layer 14 of the adhesive flange by means of an adhesive layer 16 (e.g. a rubber resin or acrylic-based adhesive) at a position radially outwardly of the joint with the inner wall 3. The inner 3 and outer 1 walls are thus connected together, albeit indirectly, in the region of the adhesive flange as well as at the peripheral margins 5.

Figure 2:
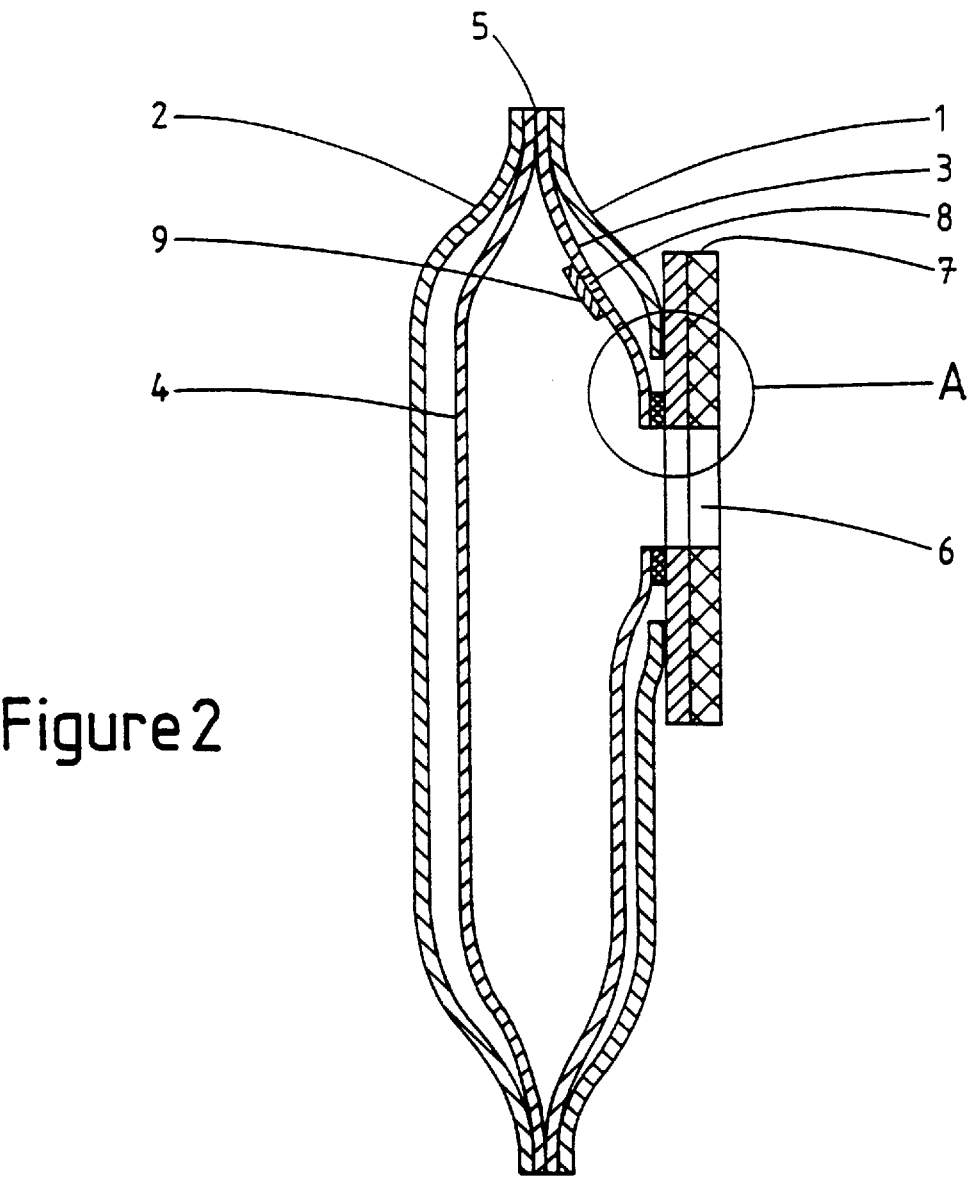
FIG. 2 is a sectional elevation along line I—I in FIG. 1.

The ostomy bag liner illustrated in FIGS. 1 to 3 can serve as the inner bag in the two-bag arrangement illustrated in WO-A-94/12128. In such a case, an outer water-impermeable bag (not shown) formed of, for example, PVC, PVDC or EVA may be secured to the PVC backing layer 14 of the adhesive flange at a position radially outwardly of the outer wall 1, 16. Such an outer bag is connected to the flange in such a way as to be peelably or frangibly detached therefrom. Preferably the outer bag (not shown) is secured to the adhesive flange by means of a peelable adhesive layer which has lower adhesive strength than any of adhesive layers 16, 13 and 12. An advantage of the ostomy bag liner of the present invention is that, with the exception of the relatively small PVC components, and some of the adhesives, the ostomy bag is fully biodegradable. This is in contrast to many of the flushable ostomy bags proposed hitherto, in which an inner layer of non-biodegradable material is employed in order to render the ostomy bag water-impermeable.

It will readily be apparent that numerous modifications and alterations may be made to the ostomy bag liner of the present invention without departing from the principles underlying the invention, and all such modifications and alterations are within the scope of this Application.

What is claimed is:

1. A biodegradable, flushable ostomy bag liner comprising:
    inner walls formed from one of a polyvinylacetate and a polyvinylalcohol film;
    outer walls formed from a non-woven fabric;
    means defining an opening in the inner and outer walls for receiving bodily waste from the stoma of a patient; and
    an adhesive flange for securing the ostomy bag liner to the body wall of a patient, the adhesive flange being secured to at least said inner wall of the liner and surrounding said opening; wherein the inner and outer walls are unconnected and form a non-laminar arrangement over a greater part of their area, but are connected together around their peripheral margins and in the region of the adhesive flange.

2. The ostomy bag liner according to claim 1 wherein the non-woven fabric is formed from biodegradable fibres.

3. The ostomy bag liner according to claim 2 wherein the biodegradable fibres comprise cellulose-based fibres.

4. The ostomy bag liner according to claim 3 wherein the cellulose-based fibres are fibres formed from rayon, cellulose acetate or cotton.

5. The ostomy bag liner according to claim 2 wherein the fibres have an average length of less than about 8 mm.

6. The ostomy bag liner according to claim 2 wherein the fibres have an average length of less than about 6 mm.

7. The ostomy bag liner according to claim 1 wherein the non-woven fabric includes a plurality of fibres and a water-soluble/water-disintegrable polymer capable of binding the fibres.

8. The ostomy bag liner according to claim 7 wherein the water-soluble/water-disintegrable polymer comprises PVA.

9. The ostomy bag liner according to claim 7 wherein the fibres are present in a ratio of at least 5:1 by weight with regard to the polymer binder.

10. An ostomy bag liner according to claim 9 wherein the fibre:polymer binder ratio is at least 10:1.

11. The ostomy bag liner according to claim 1 wherein the inner and outer walls are formed of such material, and have such thickness, as to be of substantially equivalent mechanical strength.

12. The ostomy bag liner according to claim 1 wherein the non-woven fabric is formed from synthetic fibres.

13. An ostomy bag comprising a water-impermeable, gas-impermeable outer bag and, contained therein, an ostomy bag liner as defined in any one of the preceding claims, and an adhesive flange, the outer bag and ostomy bag liner being connected together at the adhesive flange.

14. The ostomy bag liner according to claim 12 wherein the fibres have an average length of less than about 8 mm.

15. The ostomy bag liner according to claim 12 wherein the fibres have an average length of less than about 6 mm.

16. The ostomy bag liner according to claim 1, wherein said inner walls are formed from one of a polyvinylacetate and a polyvinylalcohol film of a grade which disintegrates within 60 seconds in water at 50° C., but retains its structural integrity in water at 25° C. for at least two days; and said outer walls are formed from a non-woven fabric which disintegrates in water at 25° C.

* * * * *